United States Patent [19]

Menicatti et al.

[11] Patent Number: 4,899,813
[45] Date of Patent: Feb. 13, 1990

[54] PROCESS AND APPARATUS FOR THE SYNTHESIS OF UREA AND MATERIAL USED IN IT

[75] Inventors: Sergio Menicatti, Milan; Cesare Miola, S.Donato Milanese; Franco Granelli, Milan, all of Italy

[73] Assignee: Snamprogetti S.p.A., Milan, Italy

[21] Appl. No.: 173,032

[22] Filed: Mar. 22, 1988

Related U.S. Application Data

[63] Continuation of Ser. No. 722,400, Apr. 12, 1985, abandoned.

[30] Foreign Application Priority Data

Apr. 20, 1984 [IT] Italy .................. 20635 A/84

[51] Int. Cl.⁴ ........................................ F28F 19/06
[52] U.S. Cl. ..................... 165/133; 165/180
[58] Field of Search ............... 165/133, 180, 905

[56] References Cited

U.S. PATENT DOCUMENTS

| | | | |
|---|---|---|---|
| 3,041,152 | 6/1962 | Christensen | 564/88 |
| 3,236,888 | 2/1966 | Wentworth | 564/68 |
| 3,515,520 | 6/1970 | Hervert | 422/241 |
| 4,210,600 | 7/1980 | Zardi | 564/71 |
| 4,291,104 | 9/1981 | Keifert | 422/241 |
| 4,559,207 | 12/1985 | Hiller et al. | 422/241 |

FOREIGN PATENT DOCUMENTS

| | | | |
|---|---|---|---|
| 1184004 | 6/1968 | United Kingdom . | |
| 1292515 | 3/1970 | United Kingdom . | |
| 1341497 | 4/1971 | United Kingdom . | |
| 1327321 | 8/1973 | United Kingdom | 564/71 |
| 2087381 | 8/1981 | United Kingdom . | |

Primary Examiner—Albert W. Davis, Jr.
Attorney, Agent, or Firm—Morgan & Finnegan

[57] ABSTRACT

Process and apparatus for the production of urea, wherein the carbamate decomposers and/or condensers are equipped with stainless steel tubes internally lined with zirconium.

4 Claims, 1 Drawing Sheet

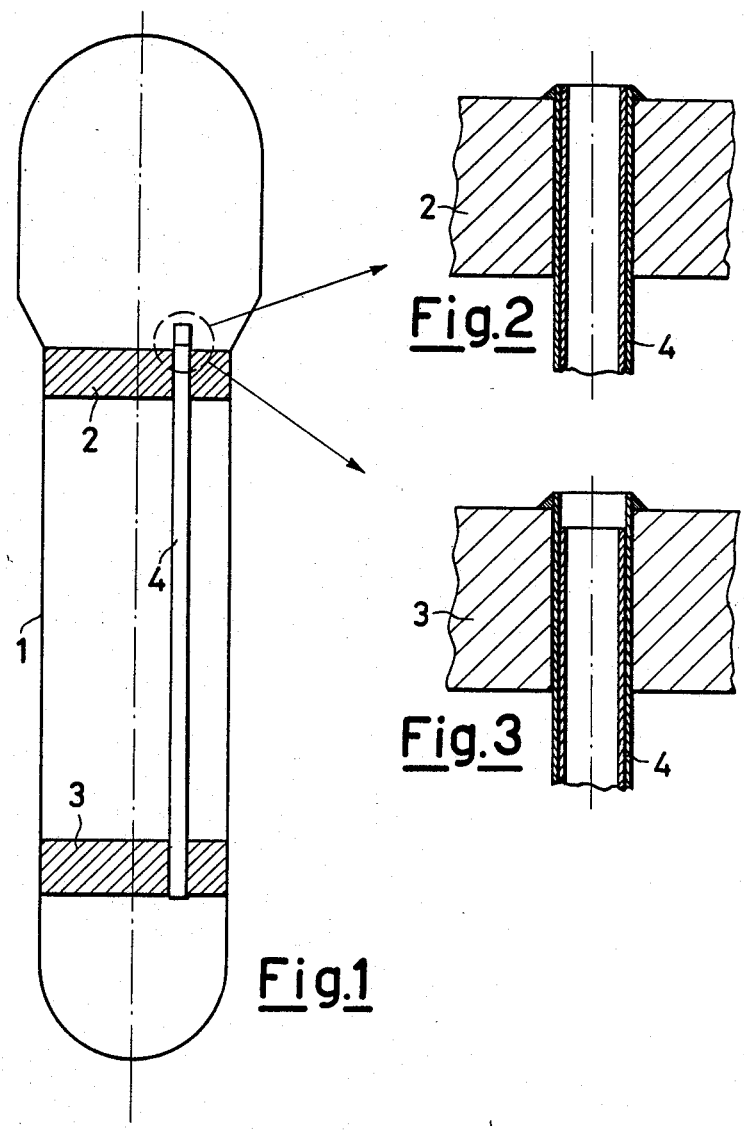

PROCESS AND APPARATUS FOR THE SYNTHESIS OF UREA AND MATERIAL USED IN IT

This is a continuation of co-pending application Ser. No. 722,400, filed on Apr. 12, 1985, now abandoned.

The present invention relates to a process for the synthesis of urea, and to a material used in it.

Many processes are known in the art for the production of urea.

In said processes ammonia and carbon dioxide are reacted in one or more reactor(s), producing an aqueous solution containing urea, ammonium carbamate not transformed into urea and the excess ammonia used in the synthesis. The ammonium carbamate is removed from the aqueous solution by means of the decomposition of said carbamate inside decomposers, under pressures which may be substantially equal to the synthesis pressure, or lower even lower than atmospheric pressure.

The decomposition is carried out in decomposers by supplying heat from the outside, by means of indirect heat exchange with a hotter fluid possibly stripping the decomposition products with inert gases, or with ammonia or carbon dioxide or mixtures of inert gases with ammonia and/or carbon dioxide; the stripping may also be accomplished by taking advantage of the excess ammonia dissolved in the urea solution (self-stripping), without supplying any stripping agent from the outside.

The products from carbamate decomposition, together with the possible stripping agents, not comprehensive of the inerts, are normally condensed within condensers. The liquid which is obtained is recycled to the synthesis reactors.

For reference purposes the following patents may be quoted: U.S. Pat. No. 4.314.077; U.K. Pat. 1.184.004; U.K. Pat. 1.292.515; U.S. Pat. No. 3.984.469; U.S. Pat. No. 4.137.262; German Pat. 2.116.267; French Pat. 2.489.323, describing processes for urea production with the hereinabove mentioned characteristics.

The most critical steps in the process operation are those wherein ammonium carbamate is at its highest concentration and at its highest temperature. In the above mentioned processes these steps coincide with the steps of ammonium carbamate decomposition (or stripping) and condensation.

The problem which has to be solved in those steps is the problem of corrosion caused by ammonium carbamate and by $CO_2$ (when used as the stripping agent or released from the decomposition of carbamate). The corrosion problems are particularly noticeable if for decomposing the carbamate and for condensing the decomposition products and possible stripping agents, pieces of equipment of the type with a vertical tube nest are used, inside which the liquid to be decomposed or condensed is distributed along the tubes.

The known art envisages for said equipment the use of titanium-plated materials and of titanium tubes, along which the fluids to be stripped or condensed or decomposed flow.

Other alternatives which are suggested by the known art are those using high-alloy austenitic and/or diphasic austenitic-ferritic steel. The use of titanium plated steel requires sophisticated machining techniques, while the use of austenitic and/or di-phasic austenitic-ferritic steels does not achieve completely satisfactory result in the regions where corrosion and thermal and mechanical stresses are higher.

It has now been surprisingly found that it is possible to overcome the drawbacks of the known art by using materials of conventional urea grade for the extratube portion of the equipment (in contact with the process fluids) and stainless steel tubes (which may also be made of the same steel as the extratube portion), internally lined with a thin foil of zirconium, not welded to the outer tube. The process according to the present invention comprises the steps of the reaction of ammonia and $CO_2$, the decomposition of ammonium carbamate the possible stripping of decomposition products (in particular causing the carbamate-containing urea solution to flow as a thin layer on the inner walls of the tubes of a vertical tube nest), the condensation of decomposition products and the recycle thereof to the reaction step. The process is characterized by the decomposer(s) of ammonium carbamate and/or the condensers comprise an extratube structure (in their portion in contact with the process fluids) of conventional urea-grade steel having a nest of stainless steel tubes (which may also be made of the same steel as the extratube portion) internally lined with a thin zirconium foil not welded to said tubes.

The zirconium-lined tubes, assembled in the decomposers and/or condensers of the process according to the present invention are manufactured by slipping zirconium tubes inside steel tubes, taking care that the difference between the inner diameter of the stainless steel tubes and the outer diameter of zirconium tubes are suitable for assembling (preferably between 0.2 and 0.5 mm); the outer stainless-steel tubes are then approached and caused to adhere to the inner zirconium tubes or vice-versa, by means of the most suitable technique (e.g., by means of a mechanical technique).

It has been surprisingly found that, besides the reduction of the cost of decomposition and condensation equipment due to the use of conventional urea-grade steel, when the zirconium is exclusively limited to a thin foil (preferably of thickness lower than 0.8 mm) in the interior of the tubes, the end junction between the outer tubes and the inner zirconium tubes is such that the carbamate does not corrode the tube junction zone. Thus, it is not necessary to weld the two metals to each other.

A further advantage of the invention, in addition to those hereinabove described, is that the tubes can be easily externally welded on to the tube plates, so that the material constituting the outer surface of the tubes is equal to or compatible with the material constituting the tube plates, and the remaining portions of the equipment.

Equipment which can be used in the process according to the present invention is schematically shown in FIGS. 1, 2 and 3 of the attached drawing.

FIG. 1 shows a carbamate stripper (1) equipped with an upper tube plate (2) and a lower tube plate (3), through which stainless steel tubes, internally lined with zirconium, pass (only one of said tubes (4) is shown).

FIGS. 2 and 3 show two different types of welding of the stainless steel outer tube.

FIG. 2 shows the welding between the outer tube and the tube plate without removing the zirconium inner tube which lines the outer tube wherein the outer tube is welded to the tube plate.

FIG. 3 shows on the contrary the welding between the outer tube and the tube plate after having removed the zirconium inner tube which lines the outer tube wherein the outer tube is welded to the tube plate.

The Examples shown in the attached drawings are not limitative of the invention.

The stainless steel which can be used for the outer tubes are preferably selected among AISI 316 L or an equivalent urea-grade steel, the 25 Cr, 22 Ni, 2 Mo urea-grade steel or austenitic and/or diphasic austenitic-ferritic steels.

The zirconium lining is preferably ASTM B523 type grade R 60702/R 60704/R 60705 or the equivalent.

Running tests carried out on strippers of industrial plants equipped with zirconium-lined tubes have shown that tubes made according to the present invention do not show any faults and in particular any corrosion phenomena after 7000 hours in a medium containing urea and carbamate.

We claim:

1. An apparatus for use in an ammonium carbamate decomposer and/or a condenser in the synthesis of urea, comprising a nest of stainless steel tubes internally lined with a foil made of unalloyed zirconium which is not welded to said stainless steel tubes, wherein the thickness of said zirconium foil is less than about 0.8 mm.

2. The apparatus of claim 1, wherein the thickness of said zirconium foil is between about 0.2 mm and about 0.5 mm.

3. The apparatus of claim 1, wherein the outer surface of said zirconium foil intimately contacts the inner surface of said stainless steel tubes.

4. The apparatus of claim 3, wherein said intimate contact is achieved by expanding said zirconium foil.

* * * * *